United States Patent
Roh et al.

(10) Patent No.: US 9,063,424 B2
(45) Date of Patent: Jun. 23, 2015

(54) ISOCYANURATE COMPOUND FOR FORMING ORGANIC ANTI-REFLECTIVE LAYER AND COMPOSITION INCLUDING SAME

(75) Inventors: Hyo-Jung Roh, Hwaseong-Si (KR); Dong-Kyu Ju, Hwaseong-Si (KR); Hyun-Jin Kim, Hwaseong-Si (KR); Deog-Bae Kim, Seoul (KR)

(73) Assignee: DONGJIN SEMICHEM CO., LTD., Incheon (KR)

( * ) Notice: Subject to any disclaimer, the term of this patent is extended or adjusted under 35 U.S.C. 154(b) by 522 days.

(21) Appl. No.: 13/393,682

(22) PCT Filed: Sep. 14, 2010

(86) PCT No.: PCT/KR2010/006281
§ 371 (c)(1),
(2), (4) Date: Mar. 1, 2012

(87) PCT Pub. No.: WO2011/031123
PCT Pub. Date: Mar. 17, 2011

(65) Prior Publication Data
US 2012/0164338 A1    Jun. 28, 2012

(30) Foreign Application Priority Data
Sep. 14, 2009   (KR) .................. 10-2009-0086352

(51) Int. Cl.
| | | |
|---|---|---|
| *G03F 7/09* | (2006.01) | |
| *C07D 251/06* | (2006.01) | |
| *C08L 81/00* | (2006.01) | |
| *H01L 31/0216* | (2014.01) | |
| *C08F 283/00* | (2006.01) | |
| *C08G 75/00* | (2006.01) | |
| *C08K 5/00* | (2006.01) | |
| *B05D 3/02* | (2006.01) | |
| *G03F 7/16* | (2006.01) | |
| *H01L 21/02* | (2006.01) | |

(Continued)

(52) U.S. Cl.
CPC .............. *G03F 7/091* (2013.01); *C07D 251/06* (2013.01); *C08L 81/00* (2013.01); *H01L 31/02168* (2013.01); *C08F 283/00* (2013.01); *C08G 75/00* (2013.01); *C08K 5/0025* (2013.01); *H01L 2924/0705* (2013.01); *B05D 3/02* (2013.01); *G03F 7/168* (2013.01); *H01L 2924/364* (2013.01); *H01L 21/0201* (2013.01); *H01L 21/4757* (2013.01); *H01L 21/0271* (2013.01); *C08K 5/42* (2013.01)

(58) Field of Classification Search
CPC ...... B05D 3/02; C07D 251/06; C08F 283/00; C08G 75/00; C08K 5/0025; C08K 5/42; C08L 81/00; G03F 7/091; G03F 7/168; H01L 21/0201; H01L 21/0271; H01L 21/4757; H01L 31/02168; H01L 2924/0705; H01L 2924/364
USPC ........ 544/222; 524/507, 590, 600; 427/372.2, 427/385.5; 525/535, 540
See application file for complete search history.

(56) References Cited

U.S. PATENT DOCUMENTS 6,414,146 B1    7/2002  Takeyama et al.
6,528,673 B2 *  3/2003  Cruse et al. .................. 556/427
(Continued)

FOREIGN PATENT DOCUMENTS

EP         1 598 702 A1     11/2005
KR    10-2006-0046423 A      5/2006
(Continued)

*Primary Examiner* — Patrick Niland
(74) *Attorney, Agent, or Firm* — Birch, Stewart, Kolasch & Birch, LLP

(57) ABSTRACT

An isocyanurate compound for forming an organic anti-reflective coating layer, which has superior stability and etch rate at a high temperature, and which has a high refractive index, is represented by following Formula 1.

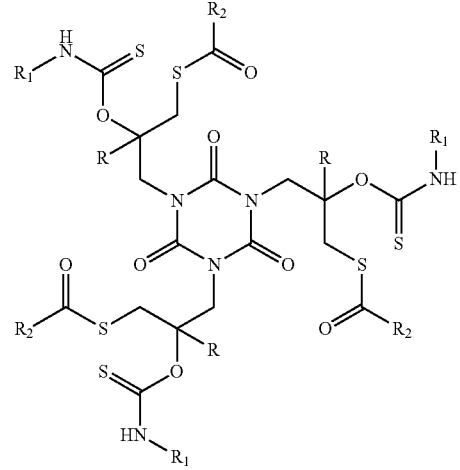

[Formula 1]

In Formula 1, R is independently a hydrogen atom or a methyl group, $R_1$ is independently a chain type or ring type saturated or unsaturated hydrocarbyl group of 1 to 15 carbon atoms containing 0 to 6 of hetero atoms, and $R_2$ independently a chain type or ring type saturated or unsaturated hydrocarbyl group of 1 to 15 carbon atoms containing 0 to 15 of hetero atoms, wherein, $R_1$ can have at least two bonding parts, and in the case that $R_1$ has at least two bonding parts, the rest parts except $R_1$ of the compounds represented by Formula 1 can connect to the $R_1$ to form a polymer structure.

4 Claims, 3 Drawing Sheets

(51) Int. Cl.
*H01L 21/4757* (2006.01)
*H01L 21/027* (2006.01)
*C08K 5/42* (2006.01)

(56) References Cited

U.S. PATENT DOCUMENTS 7,541,134 B2  6/2009  Iwabuchi et al.

2002/0161223 A1  10/2002  Takeyama et al.
2008/0138744 A1   6/2008  Hatanaka et al.
2010/0022090 A1   1/2010  Sakaguchi et al.

FOREIGN PATENT DOCUMENTS

| KR | 10-2006-0048011 A | 5/2006 |
| KR | 10-2007-0012512 A | 1/2007 |
| WO | WO 2008/069047 A1 | 6/2008 |

* cited by examiner

ISOCYANURATE COMPOUND FOR FORMING ORGANIC ANTI-REFLECTIVE LAYER AND COMPOSITION INCLUDING SAME

FIELD OF THE INVENTION

This invention relates to an isocyanurate compound for forming an organic anti-reflective coating layer and a composition including the same, and more particularly to an isocyanurate compound for forming an organic anti-reflective coating layer, which has superior stability and etch rate at a high temperature (25° C. or over), and a high refractive index, and a composition including the same.

BACKGROUNDS OF THE INVENTION

In a photolithography process, ArF (193 nm) excimer laser of short wavelength is used as the exposure light source in order to improve the marginal resolution of the photoresist pattern. However, if the wavelength of the exposure light shortens, optical interference effect by the light reflected from the etching layer of the semi-conductor substrate increases, and the pattern profile or the uniformity of thickness is deteriorated due to undercutting, notching, and so on. To overcome these problems, a bottom anti-reflective coating layer (bottom anti-reflective coatings: BARCs) is conventionally formed between the etching layer and the photoresist layer to absorb the exposure light (reflected light). The bottom anti-reflective coating layer can be classified according to used materials into the inorganic anti-reflective coating layer made of titanium, titanium dioxide, titanium nitride, chrome oxide, carbon, amorphous silicon, and so on, and the organic anti-reflective coating layer made of a polymer material. Conventionally, in comparison with the inorganic anti-reflective coating layer, the organic anti-reflective coating layer does not require complex and expensive apparatus such as a vacuum evaporator, a chemical vapor deposition (CVD) device, a sputter device and so on for forming the layer, and has a high absorptivity of a radioactive light, and low molecular weight materials does not diffuse from the organic anti-reflective coating layer into a photoresist layer during a heating, coating, and drying process, and the organic anti-reflective coating layer has an excellent etch rate in a dry etch process of a photolithography process.

U.S. Pat. No. 6,414,146 B1 of Nissan Chemical Industries, Ltd., discloses an isocyanurate compound and a method for producing the same. The isocyanurate compound has a high refractive index, and is useful as an organic anti-reflective coating layer. However, the isocyanurate compound is unstable because it has a thiol group (—SH) in its end and can form disulfide bonds at room temperature (25° C.) or over.

SUMMARY OF THE INVENTION

Therefore, it is an object of the present invention to provide an isocyanurate compound for forming an organic anti-reflective coating layer and a composition including the same, which has superior stability and etch rate at a high temperature (25° C. or over), and a high refractive index, in the photolithography process in which various radiations including ArF are used as exposure light source.

It is another object of the present invention to provide an isocyanurate compound for forming an organic anti-reflective coating layer and a composition including the same, which can improve pattern profile by preventing undercutting, notching and footing.

In order to achieve these objects, the present invention provides an isocyanurate compound for forming an organic anti-reflective coating layer represented by the following Formula 1.

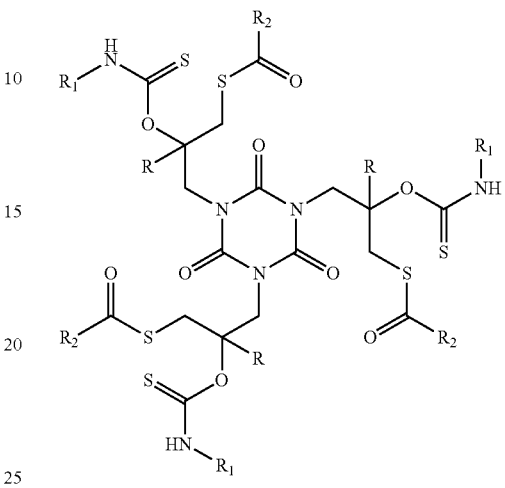

[Formula 1]

In Formula 1, R is independently a hydrogen atom or a methyl group, $R_1$ is independently a chain type or cyclic type saturated or unsaturated hydrocarbyl group of 1 to 15 carbon atoms containing 0 to 6 of hetero atoms, and $R_2$ independently a chain type or cyclic type saturated or unsaturated hydrocarbyl group of 1 to 15 carbon atoms containing 0 to 15 of hetero atoms, wherein, $R_1$ can have at least two bonding parts, and in the case that $R_1$ has at least two bonding parts, the rest parts except $R_1$ of the compounds represented by Formula 1 can connect to the $R_1$ to form a polymer structure.

The present invention also provides a composition for forming an organic anti-reflective coating layer comprising: 1 to 5 weight % of the isocyanurate compound for forming an organic anti-reflective coating layer; 0.01 to 0.25 weight % of an acid generator; 0.01 to 0.4 weight % of a crosslinking agent; and a remaining organic solvent.

By using the isocyanurate compound for forming an organic anti-reflective coating layer according to the present invention, an organic anti-reflective coating layer which has superior stability at high temperature (25° C. or over) due to capped thiol groups(—SH) of the compound, high refractive index even at the light of short wavelength of 193 nm because of its nitrogen atoms (N), sulfur atoms (S) and oxygen atoms (O), and a superior etch rate by its carbon-oxygen bonds (C—O bond), can be formed. Moreover, the k value (extinction coefficient) of an organic anti-reflective layer can be controlled by variation on the capping material for capping thiol groups (—SH), and the pattern profile can be improved by effectively preventing undercutting, notching, and footing by reflected light. Therefore, it is useful as an organic anti-reflective coating layer in a photolithography process with light source such as ArF (193 nm) excimer laser.

DETAILED DESCRIPTION OF THE INVENTION

Figure 1:
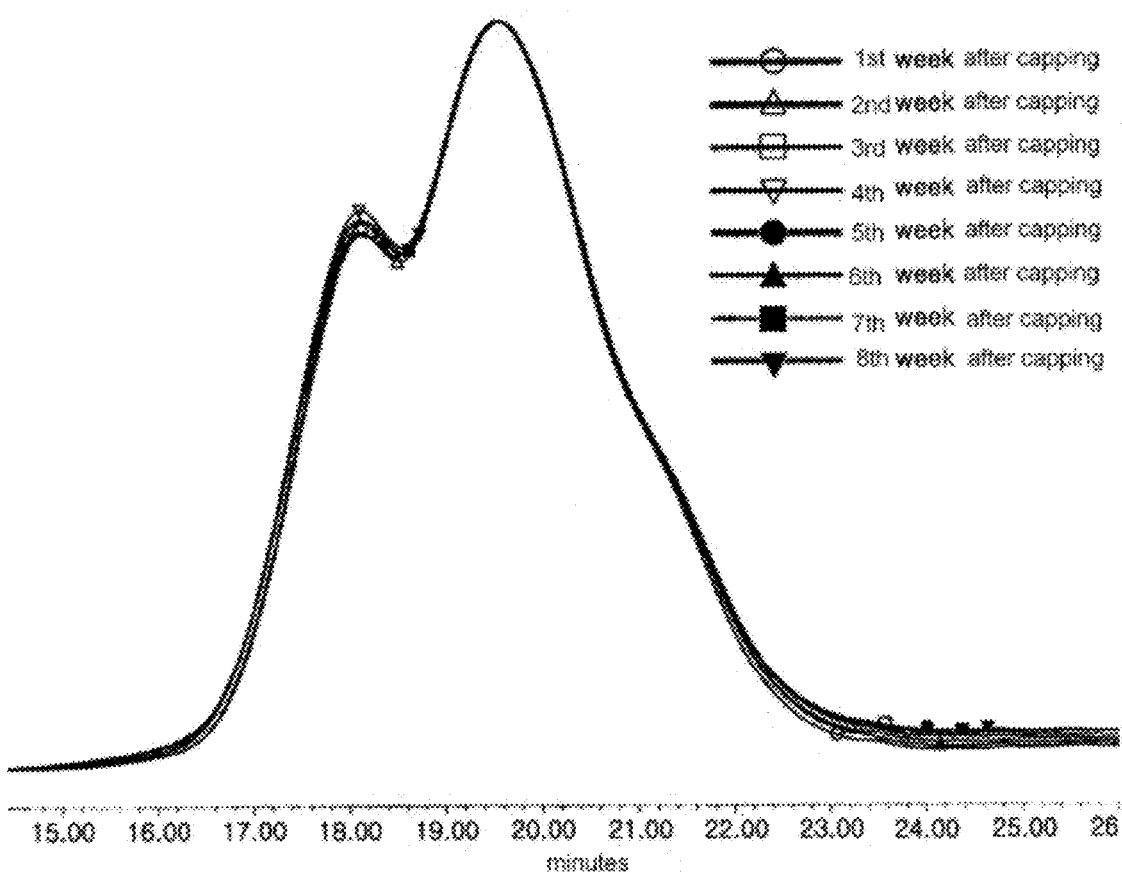
FIG. 1 is GPC graph showing the molecular weight of the isocyanurate compound represented by Formula 1a prepared by Example 1 of the present invention which is measured per week during two months.

A more complete appreciation of the invention, and many of the attendant advantages thereof, will be better appreciated by reference to the following detailed description.

An isocyanurate compound for forming an organic anti-reflective coating layer according to the present invention, which can form an organic anti-reflective coating layer between an etching layer and a photoresist layer of a semiconductor substrate, and prevent undercutting, notching, footing, and so on by absorbing the light reflected from the etching layer, is represented by following Formula 1.

[Formula 1]

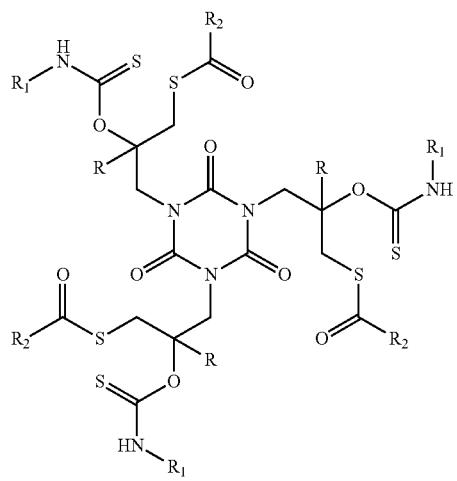

In Formula 1, R is independently a hydrogen atom or a methyl group, $R_1$ which can have at least one bonding part, is independently a chain type or cyclic type saturated or unsaturated hydrocarbyl group of 1 to 15 carbon atoms containing 0 to 6 of hetero atoms, preferably, a chain type or cyclic type saturated or unsaturated hydrocarbyl group of 1 to 10 carbon atoms containing 0 to 4 of hetero atoms such as a nitrogen atom (N), an oxygen atom (O) and/or a sulfur atom (S), and $R_2$ independently a chain type or cyclic type saturated or unsaturated hydrocarbyl group of 1 to 15 carbon atoms containing 0 to 15 of hetero atoms, preferably, a chain type or cyclic type saturated or unsaturated hydrocarbyl group of 3 to 10, more preferably 5 to 10 carbon atoms containing 0 to 8 of hetero atoms such as a nitrogen atom (N), an oxygen atom (O) and/or a sulfur atom (S).

Detailed examples of $R_1$ include

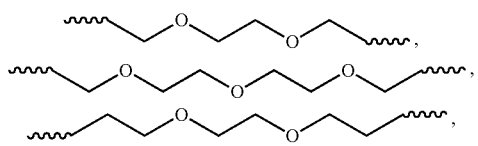

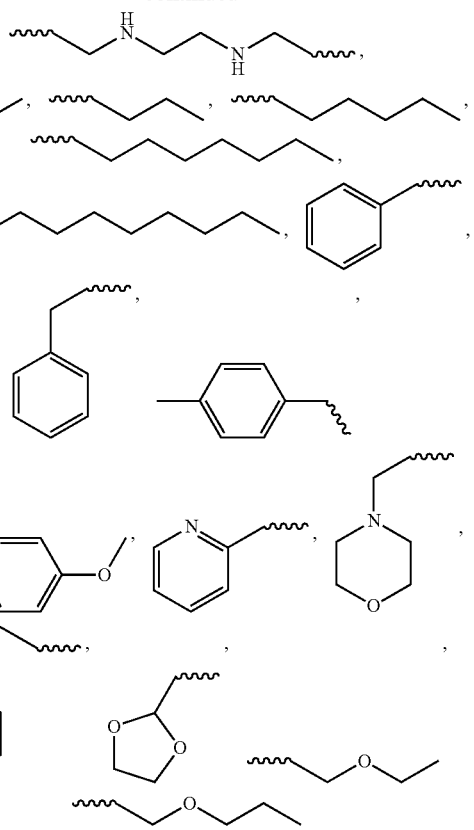

and so on (wherein, the wavy line (∿)

indicates a bonding part. Detailed examples of $R_2$ include

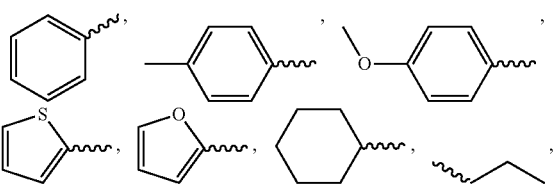

and so on (wherein, the wavy line)

indicates a bonding part). Wherein, $R_1$ can have at least two bonding parts, and in the case that $R_1$ has at least two bonding parts, the rest parts except $R_1$ of the compounds represented by Formula 1 can connect to the $R_1$ to form a polymer structure (a dimer, a trimer, and so on).

Representative examples of the isocyanurate compound represented by Formula 1 include isocyanurate compounds represented by following Formulas 1a to 1g.

[Formula 1a]
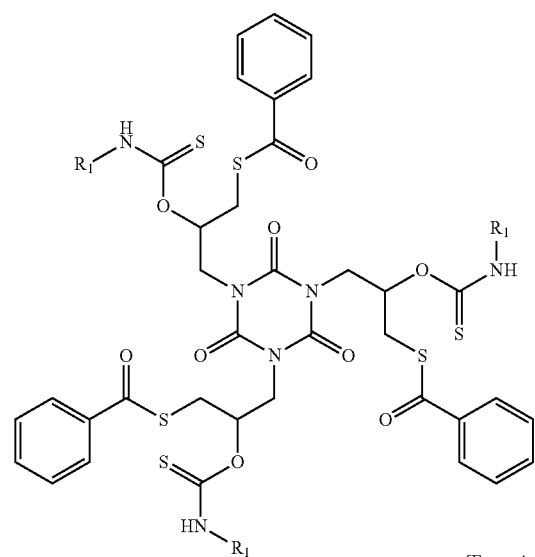
[Formula 1b]
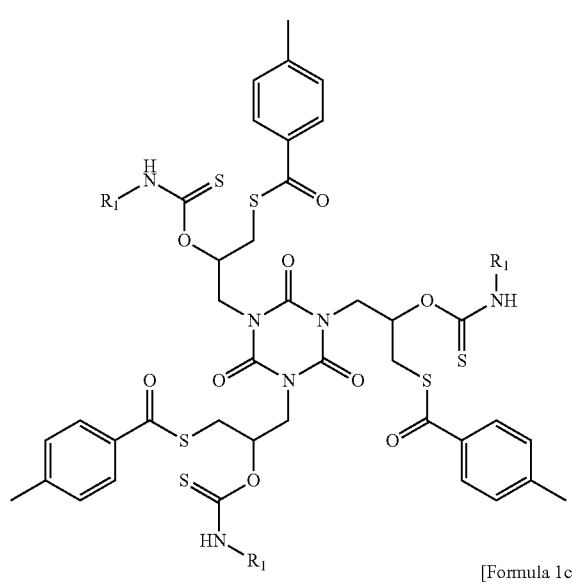
[Formula 1c]
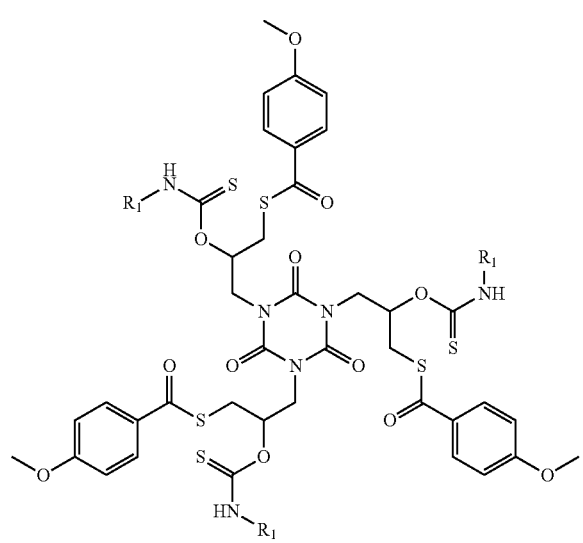
[Formula 1d]
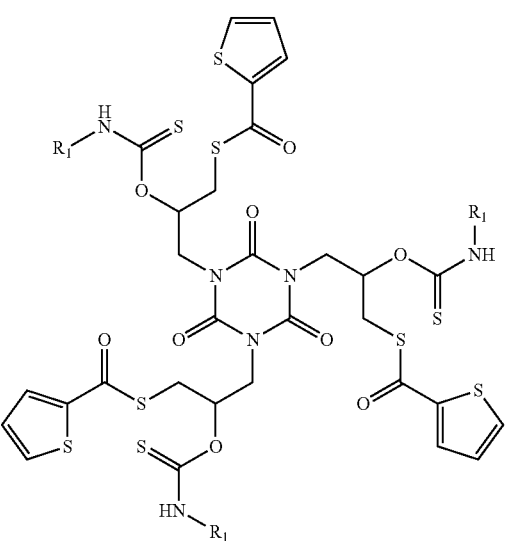
[Formula 1e]
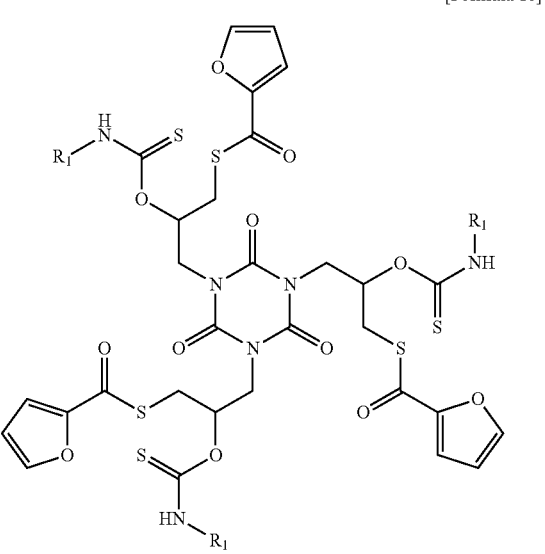
[Formula 1f]
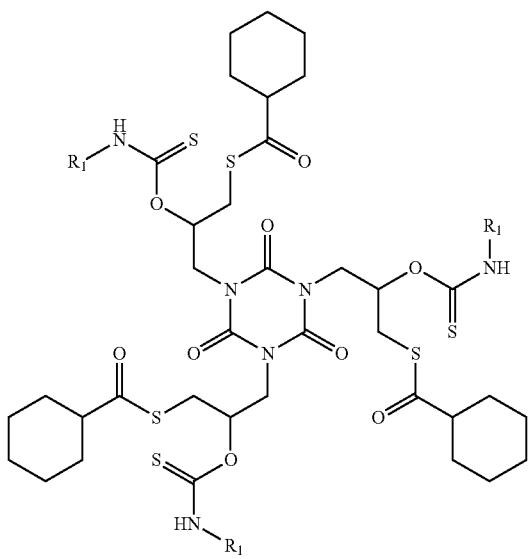

[Formula 1g]

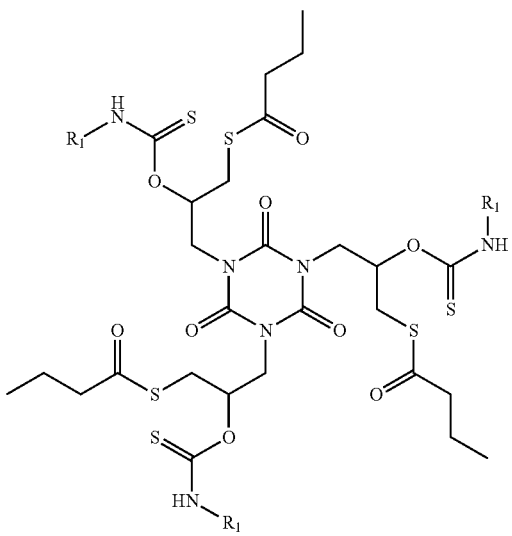

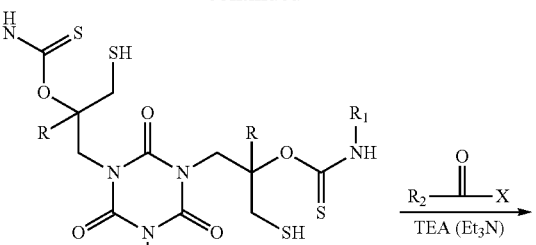

Formula 2

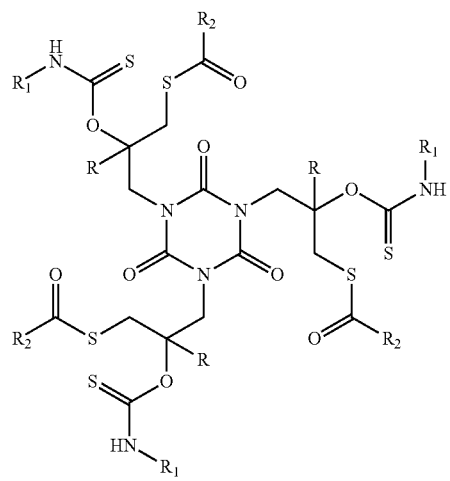

Formula 1

In Formulas 1a to 1g, $R_1$ is the same as the definition of Formula 1. Moreover, in the case that $R_1$ has at least two bonding parts, the rest parts except $R_1$ of the compounds represented by Formula 1 can independently connect to the $R_1$ to form a polymer structure.

As described in following Reaction 1, (i) tris(1,3-oxathiolane-2-thion-5-yl methyl)isocyanurate or tris(5-methyl-1,3-oxathiolane-2-thion-5-ylmethyl)isocyanurate is reacted with the compound containing at least one amine group (—NH$_2$) and $R_1$ under dimethyl formamide (DMF) at room temperature for 15 to 30 hours, to obtain the isocyanurate compound represented by following Formula 2, and (ii) the isocyanurate compound represented by following Formula 2 is dissolved in tetrahydrofuran (THF), and triethylamine (TEA) is added. Then, after lower the temperature of the reactant to 0☐, the acyl chloride or acyl bromide containing $R_2$ is added, and the reaction is performed for 20 to 40 minutes, and further reaction is performed for 10 to 24 hours at room temperature to obtain the isocyanurate compound for forming an organic anti-reflective coating layer represented by Formula 1.

In Reaction 1, R, $R_1$ and $R_2$ are the same as the definition of Formula 1, X is chlorine (Cl) or bromine (Br), and m is an integer of 1 or over, preferably 1 or 2.

Wherein, as the compound containing at least one amine group (—NH$_2$) and $R_1$ (Formula 3a)
$(R_1\text{—}(NH_2)_m)$, $H_2N$─────O─────O─────$NH_2$, (Formula 3b)
$H_2N$─────O─────O─────O─────$NH_2$, (Formula 3c)
$H_2N$─────O─────O─────$NH_2$, (Formula 3d)
$H_2N$─────NH─────NH─────$NH_2$, (Formula 3e)
$H_2N$─────, (Formula 3f)
$H_2N$─────,

[Reaction 1]

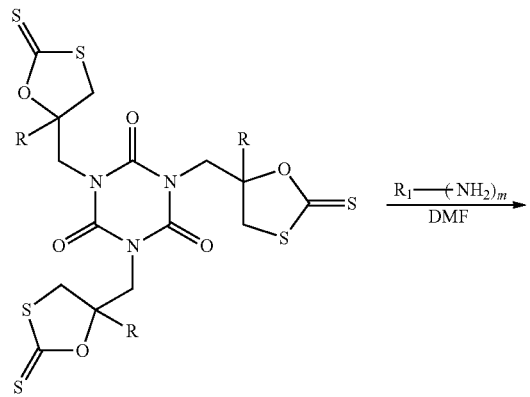

or mixtures thereof can be used. And, in the case that the compound whose m is 2 or over exist, at least two tris(1,3-oxathiolane-2-thion-5-yl methyl)isocyanurate or tris(5-methyl-1,3-oxathiolane-2-thion-5-ylmethyl)isocyanurate can react with the compound and the isocyanurate compounds represented by Formula 1 and Formula 2 can have a polymer structure.

Detailed Examples of acyl chloride or acyl bromide containing $R_2$ and so on (in Formulas 4a to 4g, X is chlorine (Cl) or bromine (Br)).

The composition for forming an organic anti-reflective coating layer according to the present invention comprises the isocyanurate compound for forming an organic anti-reflective coating layer, a crosslinking agent, an acid generator, and an organic solvent.

As the isocyanurate compound for forming an organic anti-reflective coating layer used in the present invention, a polymer type, which is formed from the compound containing $R_1$ containing at least two amine group or formed by a reaction by the crosslinking agent during the process for forming an organic anti-reflective coating layer, is preferable. Here, the weight average molecular weight (Mw) of the isocyanurate compound is 2,000 to 10,000, preferably 4,000 to 8,000. If the weight average molecular weight is less than 2,000, the organic anti-reflective coating layer may be dissolved by a photoresist solvent. If the weight average molecular weight is more than 10,000, the solubility of the compound to a solvent and the etch rate of the organic anti-reflective coating layer in a dry etch process may decrease.

The amount of the isocyanurate compound for forming an organic anti-reflective coating layer is 1 to 5 weight %, preferably 2 to 4 weight %. If the amount of the compound is less than 1 weight %, the organic anti-reflective coating layer may not be formed. If the amount of the compound is more than 5 weight %, the physical property such as the uniformity of the formed organic anti-reflective coating layer and so on, may be deteriorated.

The crosslinking agent used in the present invention crosslinks the isocyanurate compounds for forming an organic anti-reflective coating layer to form polymers and an organic anti-reflective coating layer. As the crosslinking agent, a conventional crosslinking agent, for example, a melamine type crosslinking agent and so on, can be used. The amount of the crosslinking agent is 0.01 to 0.4 weight %, preferably, 0.05 to 0.3 weight %. If the amount of the acid generator is less than 0.01 weight %, an organic anti-reflective coating layer may not be formed. If the amount of the acid generator is more than 0.4 weight %, footing may be generated on pattern profile.

The acid generator used in the present invention is to promote crosslinking reaction of the isocyanurate compound for forming an organic anti-reflective coating layer. As the acid generator, the conventional acid generators, for example, sulfonium salt type compounds, iodonium salt type compounds, mixtures thereof, and so on, preferably, triphenylsulfonium nonaflate, dodecylbenzensulfonic acid, paratoluenesulfonic acid, and so on, can be used. The amount of the acid generator is 0.01 to 0.25 weight %, preferably 0.05 to 0.2 weight %. If the amount of the acid generator is less than 0.01 weight %, an organic anti-reflective coating layer may not be formed. If the amount of the acid generator is more than 0.25 weight %, the apparatus may be contaminated due to fumes generated during a heating process.

As the organic solvent used in the present invention, the conventional organic solvents for the composition for forming an organic anti-reflective coating layer can be used. Exemplary organic solvents include, but are not limited to, cyclohexanone, cyclopentanone, butyrolactone, dimethylacetamide, dimethylformamide, dimethylsulfoxide, N-methylpyrrolidone (NMP), tetrahydro furfural alcohol, propylene glycol monomethyl ether (PGME), propylene glycol monomethyl ether acetate (PGMEA), ethyl lactate, mixtures thereof, and so on. The amount of the organic solvent should be enough to dissolve the composition for forming an organic anti-reflective coating layer, as much as the rest (94.35 to 98.98 weight %) except for the isocyanurate compound for forming an organic anti-reflective coating layer, the crosslinking agent and the acid generator, with respect to 100 weight % of the total composition for forming an organic anti-reflective coating layer.

The organic anti-reflective coating layer according to the present invention can be formed by carrying the step of coating the composition for forming an organic anti-reflective coating layer on an etching layer such as silicon wafer and aluminum substrate, and the step of crosslinking the composition for forming an organic anti-reflective coating layer coated on the etching layer. The step of coating the composition for forming an organic anti-reflective coating layer can be performed by a conventional method such as spin coating, roller coating, and so on, and the step of crosslinking the coated composition for forming an organic anti-reflective coating layer can be performed by heating with an apparatus such as a high temperature plate, a convection oven, and so on. The heating temperature for the crosslinking is 90 to 240□, preferably 150 to 210□. If the heating temperature is less than 90□, the organic solvent in the composition for forming the organic anti-reflective coating layer may not be removed sufficiently, and the crosslinking reaction may not be carried out sufficiently. If the heating temperature is more than 240□, the organic anti-reflective coating layer and the composition for forming the same may become chemically unstable.

Hereinafter, the preferable examples are provided for better understanding of the present invention. However, the present invention is not limited by the following examples.

EXAMPLE 1

Preparation of the Isocyanurate Compound Represented by Formula 1a

A. Preparation of the Isocyanurate Compound Represented by Formula 5

5 g (0.0095 mol) of tris(1,3-oxathiolane-2-thion-5-ylmethyl)isocyanurate, 1.41 g (0.0095 mol) of the compound represented by Formula 3a

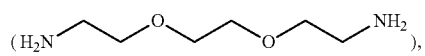

3.46 g (0.0285 mol) of the compound represented by Formula 3l

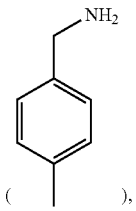

and 55.91 g of dimethyl formamide (DMF) were added into a reactor, and reacted with stirring for 24 hours at room temperature (25° C.) to obtain the isocyanurate compound represented by following Formula 5 (in Formula 5, $R_1$ is

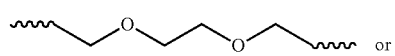

-continued

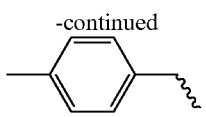

(mole ratio in the total compound:

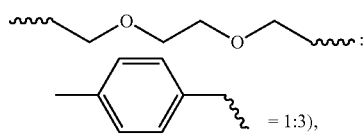

and if
R₁ is

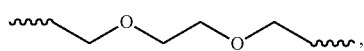

the other two except $R_1$ of the isocyanurate compound represented by Formula 5 were connected to

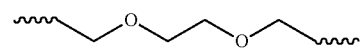

and formed a polymer. Yield: 85%, molecular weight (Mw): 4,905, polydispersity index (PDI): 1.83).

[Formula 5]

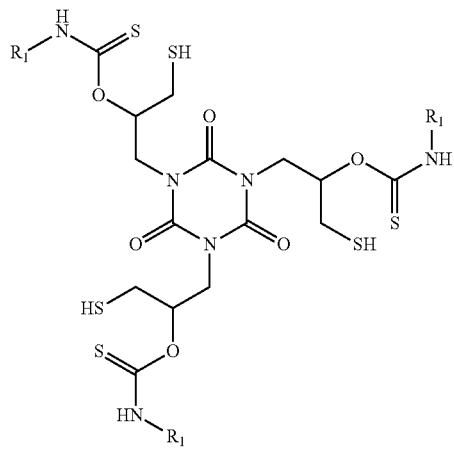

B. Preparation of the Isocyanurate Compound Represented by Formula 1a 76.29 g of tetrahydrofuran (THF) was added into a reactor (250 ml round bottomed flask), and 10 g of the isocyanurate compound represented by Formula 5 was added and dissolved, and 3.96 g of triethylamine (TEA) was added, and the temperature of the solution was lowered to 0□ using an ice-bath. 5.48 g of the compound represented by Formula 4a

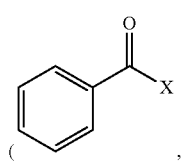

X is chlorine (Cl)) was slowly added in the solution, and reacted for 30 minutes, and further reacted for 15 hours after removing the ice bath. After the completion of the reaction, solid was filtrated. And the rest solution was precipitated in diethyl ether followed by filtration and dry to obtain the isocyanurate compound represented Formula 1a (in Formula 1a, $R_1$ is

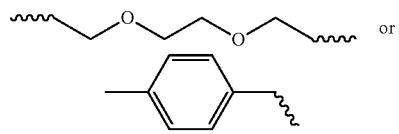

(mole ratio in the total compound:

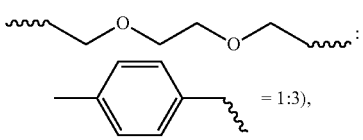

and if $R_1$ is

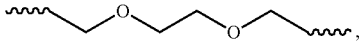

the other two except $R_1$ of the isocyanurate compound represented by Formula 1a were connected to

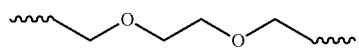

and formed a polymer. Yield: 69.8%, molecular weight (Mw): 5,241, polydispersity index (PDI): 1.84).

EXAMPLE 2

Preparation of the Isocyanurate Compound Represented by Formula 1b

Except for using 6.03 g of the compound represented by Formula 4b

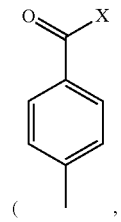

X is chlorine (Cl)) instead of 5.48 g of the compound represented by Formula 4a

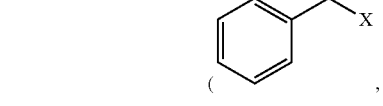

X is chlorine (Cl)), the isocyanurate compound represented by Formula 1b was prepared by the same manner described in Example 1 (in Formula 1b, $R_1$ is

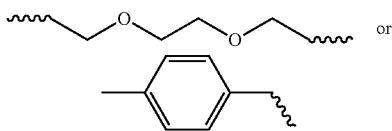 or (mole ratio in the total compound:

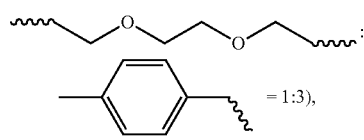 = 1:3), and if $R_1$ is

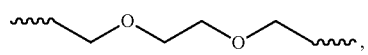, the other two except $R_1$ of the isocyanurate compound represented by Formula 1b were connected to

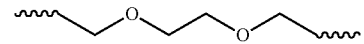

and formed a polymer. Yield: 73.0%, molecular weight (Mw): 5,581, polydispersity index (PDI): 1.83).

EXAMPLE 3

Preparation of the Isocyanurate Compound Represented by Formula 1c

Except for using 6.65 g of the compound represented by Formula 4c

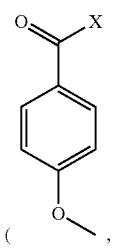,

X is chlorine (Cl)) instead of 5.48 g of the compound represented by Formula 4a

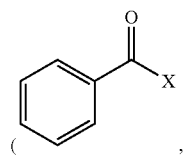,

X is chlorine (Cl)), the isocyanurate compound represented by Formula 1c was prepared by the same manner described in Example 1 (in Formula 1c, $R_1$ is

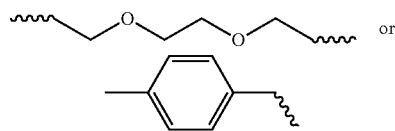 or (mole ratio in the total compound:

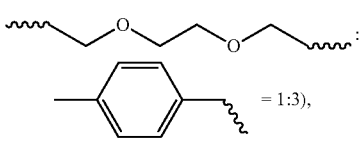 = 1:3), and if $R_1$ is

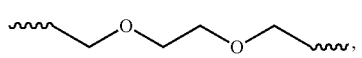, the other two except $R_1$ of the isocyanurate compound represented by Formula 1c were connected to

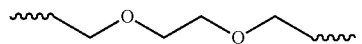

and formed a polymer. Yield: 66.7%, molecular weight (Mw): 5,751, polydispersity index (PDI): 1.80).

EXAMPLE 4

Preparation of the Isocyanurate Compound Represented by Formula 1d

Except for using 5.74 g of the compound represented by Formula 4d

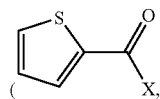,

X is chlorine (Cl)) instead of 5.48 g of the compound represented by Formula 4a

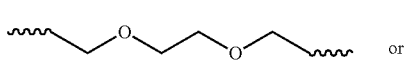,

X is chlorine (Cl)), the isocyanurate compound represented by Formula 1d was prepared by the same manner described in Example 1 (in Formula 1d, $R_1$ is

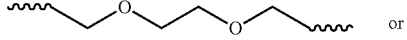 or

-continued

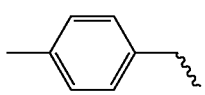

(mole ratio in the total compound:

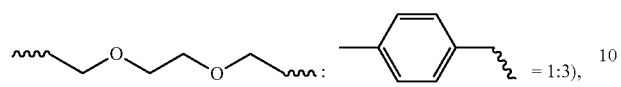 = 1:3), and if $R_1$ is

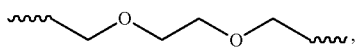, the other two except $R_1$ of the isocyanurate compound represented by Formula 1d were connected to

and formed a polymer. Yield: 71.8%, molecular weight (Mw): 5,336, polydispersity index (PDI): 1.86).

EXAMPLE 5

Preparation of the Isocyanurate Compound Represented by Formula 1e

Except for using 5.11 g of the compound represented by Formula 4e

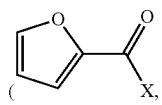

X is chlorine (Cl)) instead of 5.48 g of the compound represented by Formula 4a

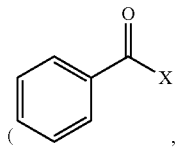

X is chlorine (Cl)), the isocyanurate compound represented by Formula 1e was prepared by the same manner described in Example 1 (in Formula 1e, $R_1$ is

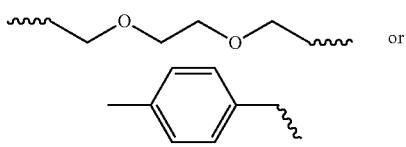 or (mole ratio in the total compound:

 = 1:3), and if $R_1$ is

, the other two except $R_1$ of the isocyanurate compound represented by Formula 1e were connected to

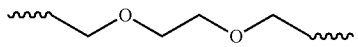

and formed a polymer. Yield: 78.6%, molecular weight (Mw): 5,121, polydispersity index (PDI): 1.81).

EXAMPLE 6

Preparation of the Isocyanurate Compound Represented by Formula 1f

Except for using 5.74 g of the compound represented by Formula 4f

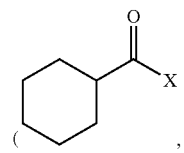

X is chlorine (Cl)) instead of 5.48 g of the compound represented by Formula 4a

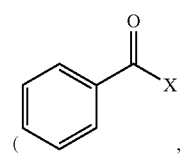

X is chlorine (Cl)), the isocyanurate compound represented by Formula 1f was prepared by the same manner described in Example 1 (in Formula 1f, $R_1$ is

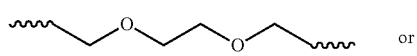 or

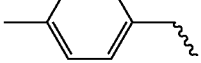

(mole ratio in the total compound:

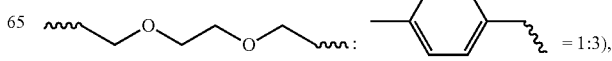 = 1:3), and if $R_1$ is

[structure: ~~~O~~O~~~], the other two except $R_1$ of the isocyanurate compound represented by Formula 1f were connected to

[structure: ~~~O~~O~~~]

and formed a polymer. Yield: 62.2%, molecular weight (Mw): 4,908, polydispersity index (PDI): 1.90.

EXAMPLE 7

Preparation of the Isocyanurate Compound Represented by Formula 1g

Except for using 4.16 g of the compound represented by Formula 4g

[structure with X=O and ring, X is chlorine (Cl)]

instead of 5.48 g of the compound represented by Formula 4a

[structure: benzoyl chloride with X]

X is chlorine (Cl)), the isocyanurate compound represented by Formula 1g was prepared by the same manner described in Example 1 (in Formula 1g, $R_1$ is

[structure: ~~~O~~O~~~] or [structure: para-substituted phenyl-CH2]

(mole ratio in the total compound:

[structure: ~~~O~~O~~~] : [phenyl-CH2] = 1:3), and if $R_1$ is

[structure: ~~~O~~O~~~], the other two except $R_1$ of the isocyanurate compound represented by Formula 1g were connected to

[structure: ~~~O~~O~~~]

and formed a polymer. Yield: 62.2%, molecular weight (Mw): 5,218, polydispersity index (PDI): 1.84.

COMPARATIVE EXAMPLE 1

Preparation of the Isocyanurate Compound Represented by Formula 5

The isocyanurate compound represented by Formula 5 was prepared by the same manner described in the step A of Example 1.

EXAMPLE 8

Stability Test of the Isocyanurate Compound

Figure 2:
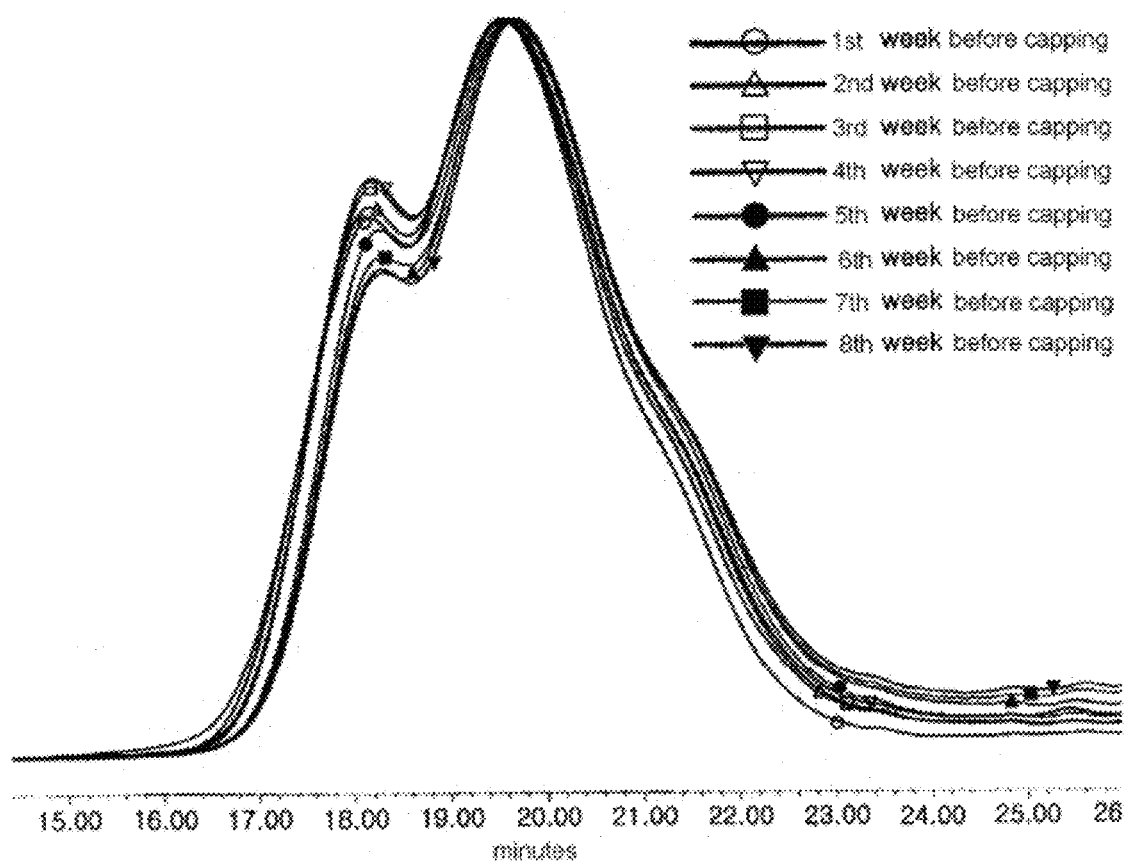
FIG. 2 is GPC graph showing the molecular weight of the isocyanurate compound represented by Formula 5 prepared by Comparative Example 1 of the present invention which is measured per week during two months.

The isocyanurate compound represented by Formula 1a prepared in Example 1 (capped compound) and the isocyanurate compound represented by Formula 5 prepared in Comparative Example 1 (uncapped compound) were preserved under high temperature (40□) for two months, and the molecular weight of them was measured using GPC (Gel Permeation Chromatography) per week. The stability of each isocyanurate compound was evaluated by observing the change of their molecular weight with time. Following FIG. 1 and FIG. 2 are GPC graphs showing the molecular weight of the isocyanurate compounds represented by Formulas 1a and 5 measured per week during two months.

EXAMPLES 9 to 15 and COMPARATIVE EXAMPLE 2

Preparation of the Composition for Forming an Organic Anti-Reflective Coating Layer, and Formation and Test of an Organic Anti-Reflective Coating Layer A. Preparation of Compositions for Forming the Organic Anti-Reflective Coating Layer As the following Table 1, 3 weight % of one of the isocyanurate compounds (Formulas 1a to 1g) prepared in Examples 1 to 7 or a copolymer(styrene: methyl methacrylate(MMA): hydroxyethyl methacrylate(HEMA)=40:30:30, Molecular weight (Mw)=15,000, Polydispersity index (PDI)=1.8), 0.2 weight % of PL 1174 (manufacturer: Cytec Industries Inc.) as a crosslinking agent and 0.1 weight % of triphenylsulfonium nonaflate were dissolved in 96.7 weight % of cyclohexanone, and stirred to obtain compositions for forming the organic anti-reflective coating layer.

B. Formation of the Organic Anti-Reflective Coating Layer

The composition for forming an organic anti-reflective coating layer was spin-coated on the etching layer of a silicon wafer, and baked at 200□ for 60 seconds to form an organic anti-reflective coating layer of 240 Å thickness.

C. Test of the Organic Anti-Reflective Coating Layer

The organic anti-reflective coating layer was etched by dry etching gas ($CF_4$) for 13 seconds using dielectric etcher (Maker: Lam research, Device name: Exelan HPT) to measure the etch rate (nm/sec) of the organic anti-reflective coating layer, and the refractive index and extinction coefficient (k value) were measured using an ellipsometer (Maker: J. A. Woolam, Device name: VUV-303). The results were represented as following Table 1.

TABLE 1

| | Isocyanurate compound | Crosslinking agent | Acid generator | Solvent | Refractive index | Extinction coefficient | Etch rate |
|---|---|---|---|---|---|---|---|
| Example 9 | Formula 1a 3 weight % | PL 1174 0.2 weight % | Triphenyl sulfonium nonaflate 0.1 weight % | Cyclo hexanone 96.7 weight % | 1.96 | 0.42 | 12.8 |
| Example 10 | Formula 1b 3 weight % | | | | 1.97 | 0.43 | 12.5 |
| Example 11 | Formula 1c 3 weight % | | | | 1.96 | 0.42 | 13.4 |
| Example 12 | Formula 1d 3 weight % | | | | 1.98 | 0.40 | 14.0 |
| Example 13 | Formula 1e 3 weight % | | | | 1.97 | 0.39 | 13.6 |
| Example 14 | Formula 1f 3 weight % | | | | 1.97 | 0.29 | 14.2 |
| Example 15 | Formula 1g 3 weight % | | | | 1.96 | 0.28 | 14.5 |
| Comparative Example 2 | Copolymer 3 weight % | | | | 1.72 | 0.46 | 4.1 |

EXAMPLES 16 to 22 and COMPARATIVE EXAMPLE 3]

Formation and Test of Photoresist Pattern

After formation of a 240 Å-thick organic anti-reflective coating layer on the etching layer of a silicon wafer by the same methods as the Examples 9 to 15 and Comparative Example 2, the photoresist composition comprising 5 g of photosensitive polymer

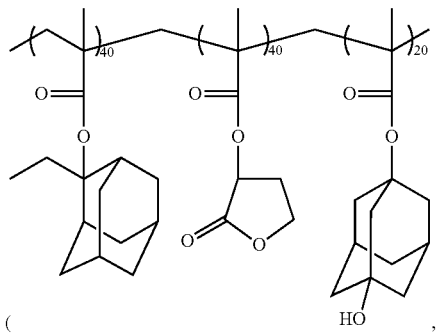

Mw=8,500, PDI=1.85), 0.2 g of triphenylsulfonium nonaplate, 0.02 g of trioctyl amine and 100 g of propylene glycol monomethyl ether acetate was coated with 1,500 Å thickness on the resulting organic anti-reflective coating layer, and soft-baked at 110☐ for 60 seconds.

Then, it was exposed using an exposure mask with line and space (L/S) patterns and a 193 nm ArF exposure equipment (ASML 1200B, 0.85NA), and post-baked at 110☐ for 60 seconds. And it was developed by 2.38 wt % of aqueous TMAH (tetramethylammonium hydroxide) to form 1:1 line and space (L/S) patterns of 65 nm line width. Electron microscope photographs of photoresist patterns by Example 16 and Comparative Example 3 were represented as FIG. 3 and FIG. 4. Results of Example 17 to 22 are similar to the result of Example 16.

As shown in FIG. 1 and FIG. 2, the isocyanurate compound for forming an organic anti-reflective coating layer according to the present invention (Formula 1a, Example 1) has steady GPC graphs in spite of time change, that is, the stability of the compound is superior. And the isocyanurate compound represented by Formula 5 (Comparative Example 1) has GPC graphs changed by time, that is, the stability of the compound is low.

The isocyanurate compound represented by Formula 5 has thiol groups (—SH) and can form disulfide bonds under room temperature (25° C.), so that the stability is lowered. But the isocyanurate compound represented by Formula 1a prepared by capping thiol groups (—SH) of the compound represented by Formula 5 loses its reaction site and has stability even at room temperature (25° C.) or over.

Figure 3:
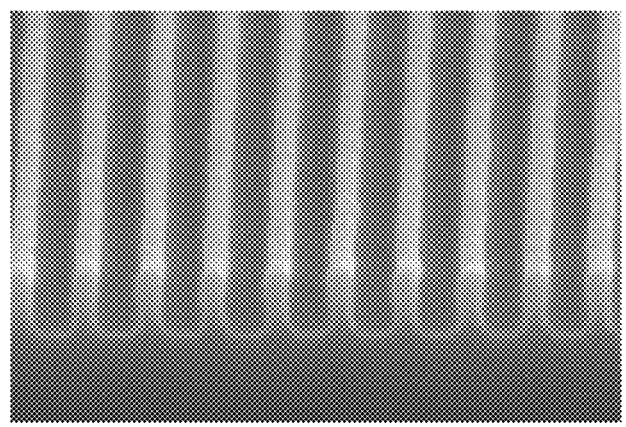
FIG. 3 is the electron microscope photograph of photoresist patterns formed by Example 16 of the present invention.
Figure 4:
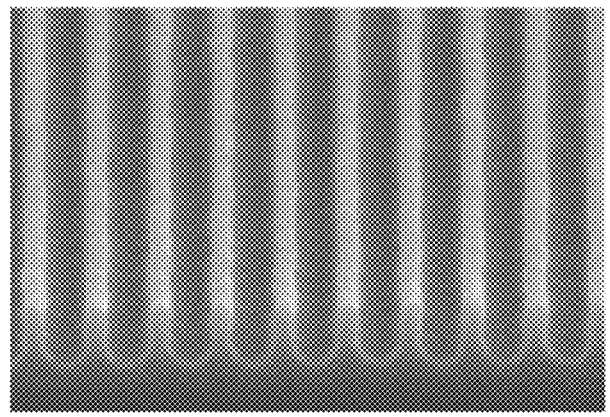
FIG. 4 is the electron microscope photograph of photoresist patterns formed by Comparative Example 3 of the present invention.

Moreover, by using the isocyanurate compound for forming an organic anti-reflective coating layer according to the present invention, an organic anti-reflective coating layer can be formed, which has high refractive index even at the light of short wavelength of 193 nm because of its nitrogen atoms (N), sulfur atoms (S) and oxygen atoms (O), and a superior etch rate as shown in Table 1. Moreover, the k value (extinction coefficient) of an organic anti-reflective layer can be controlled by variation on the capping material for capping thiol groups (—SH), and as shown in FIG. 3 and FIG. 4, the pattern profile can be improved by effectively preventing undercutting, notching, and footing by reflected light.

Therefore, the isocyanurate compound for forming an organic anti-reflective coating layer according to the present invention is useful as a composition for forming an organic anti-reflective coating layer in a photolithography process with exposure light source such as ArF (193 nm) excimer laser.

The invention claimed is:
1. An organic anti-reflective coating layer formed between an etchine layer and a photoresist layer of a semi-conductor substrate, formed with an isocyanurate compound represented by the following Formula 1,

[Formula 1]

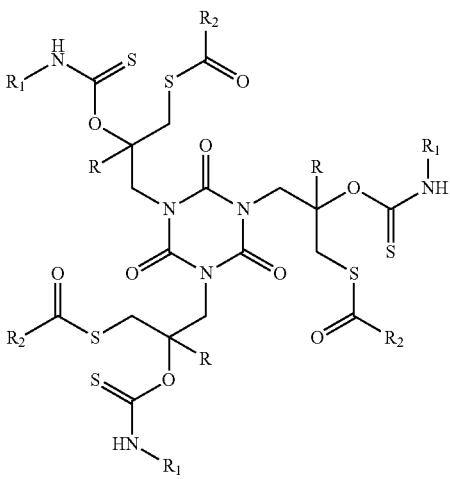

In Formula 1, R is independently a hydrogen atom or a methyl group, $R_1$ is independently a chain type or ring type saturated or unsaturated hydrocarbyl group of 1 to 15 carbon atoms containing 0 to 6 of hetero atoms, and $R_2$ independently a chain type or ring type saturated or unsaturated hydrocarhyl group of 1 to 15 carbon atoms containing 0 to 15 of hetero atoms, wherein, $R_1$ optionally has at least two bonding parts, and in the case that $R_1$ has at least two bonding parts, the rest parts, except $R_1$ of the compounds represented by Formula 1, optionally connect to the $R_1$ to form a polymer structure.

2. The organic anti-reflective coating layer of claim 1, wherein the isocyanurate compound for forming organic anti-reflective coating layer is selected from the group consisting of compounds represented by following Formulas 1a to 1g,

[Formula 1a]

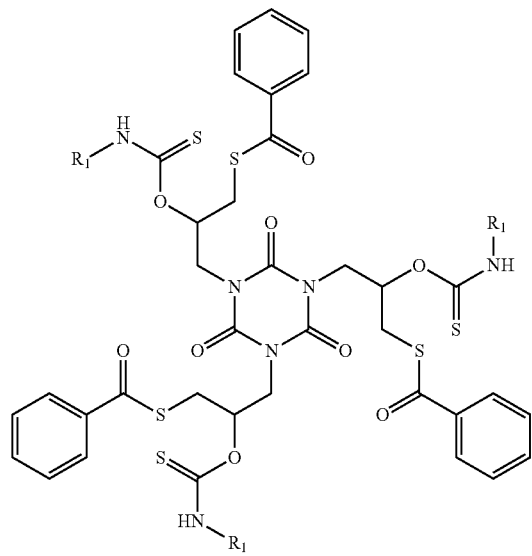

[Formula 1b]

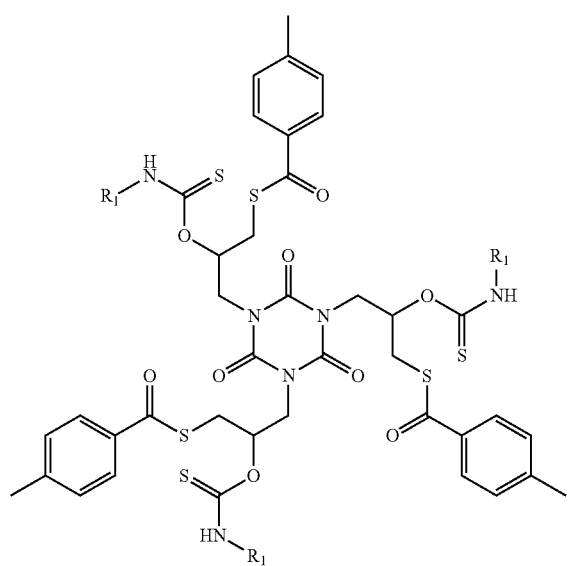

[Formula 1c]

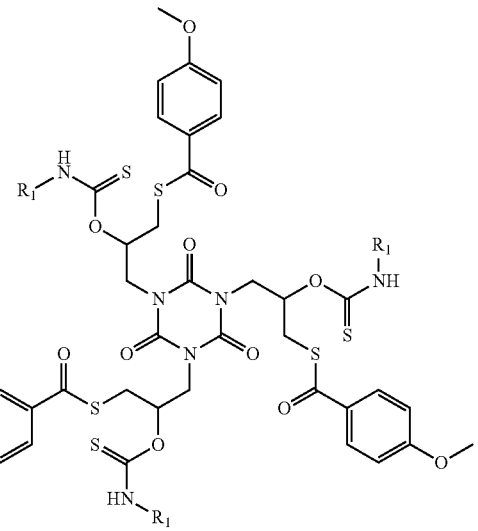

[Formula 1d]

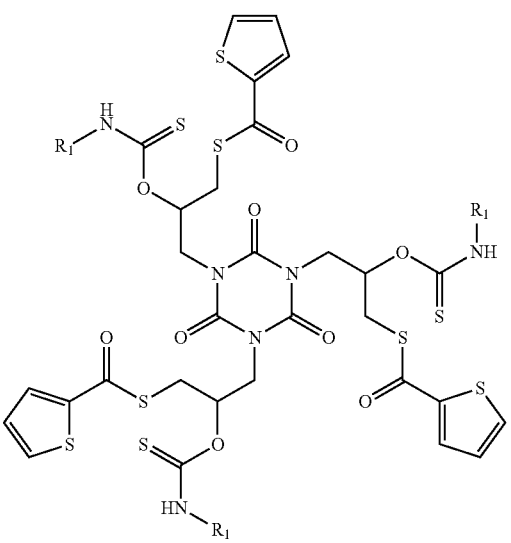

[Formula 1e]

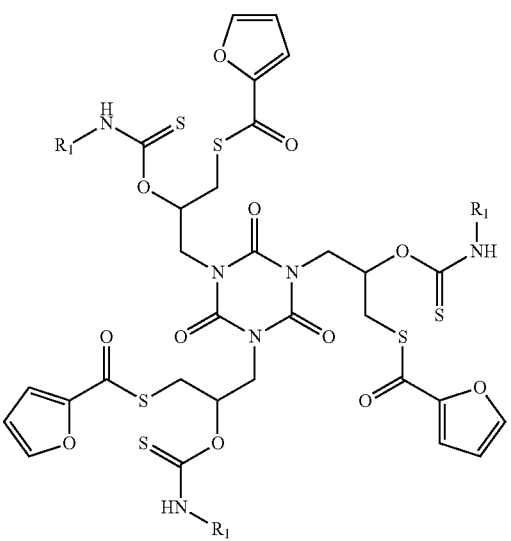

-continued

[Formula 1f]

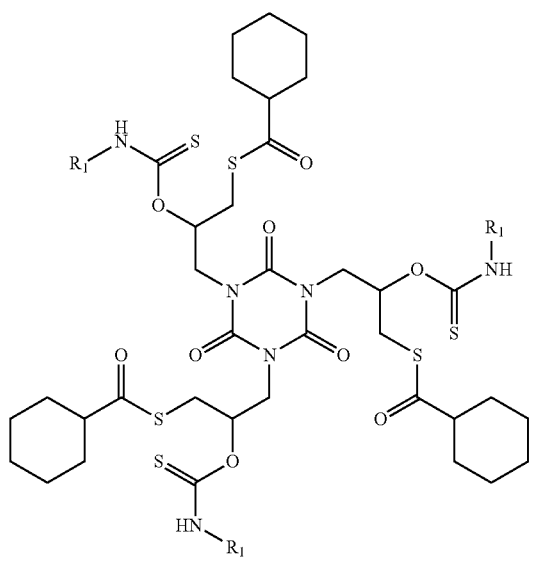

[Formula 1g]

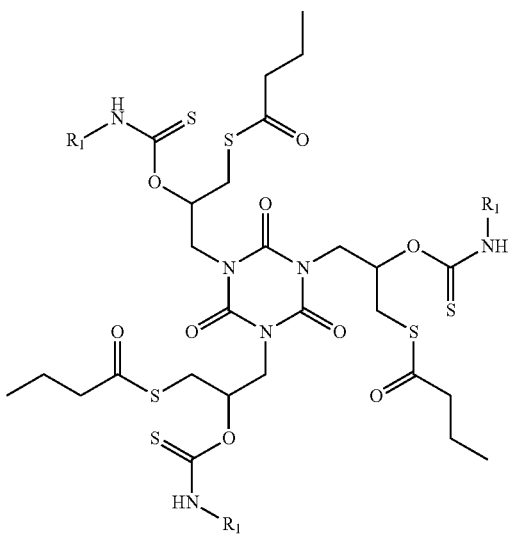

In Formulas 1a to 1g, $R_1$ is the same as the definition of Formula 1.

3. A composition for forming an organic anti-reflective coating layer, comprising:

1 to 5 weight % of an isocyanurate compound for forming an organic anti-reflective coating layer represented by the following Formula 1,

[Formula 1]

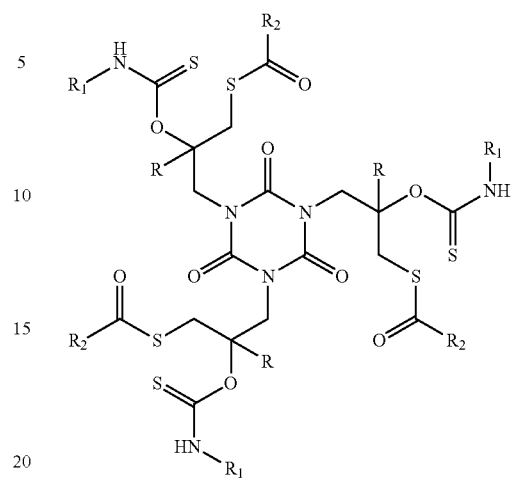

In Formula 1, R is independently a hydrogen atom or a methyl group, $R_1$ is independently a chain type or ring type saturated or unsaturated hydrocarbyl group of 1 to 15 carbon atoms containing 0 to 6 of hetero atoms, and $R_2$ independently a chain type or ring type saturated or unsaturated hydrocarbyl group of 1 to 15 carbon atoms containing 0 to 15 of hetero atoms, wherein, $R_1$ optionally has at least two bonding parts, and in the case that $R_1$ has at least two bonding parts, the rest parts except $R_1$ of the compounds represented by Formula 1 optionally connect to the $R_1$ to form a polymer structure;

0.01 to 0.4 weight % of a crosslinking agent;

0.01 to 0.25 weight % of an acid generator; and a remaining organic solvent.

4. A method for forming an organic anti-reflective coating layer, comprising the step of:

coating a composition for forming an organic anti-reflective coating layer on an etching layer, wherein the composition comprises 1 to 5 weight% of an isocyanurate compound for forming an organic anti-reflective coating layer represented by the following Formula 1, 0.01 to 0.4 weight % of a crosslinking agent, 0.01 to 0.25 weight % of an acid generator, and a remaining organic solvent,

[Formula 1]

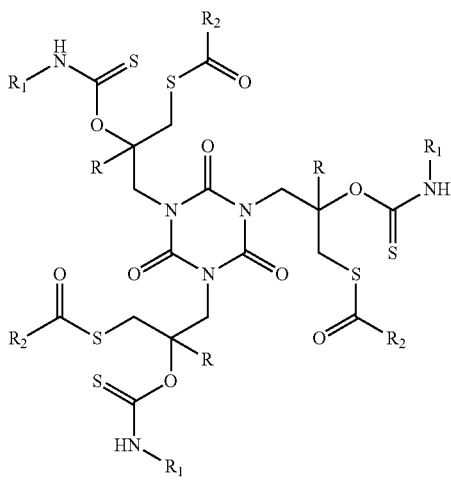

In Formula 1, R is independently a hydrogen atom or a methyl group, $R_1$ is independently a chain type or ring type saturated or unsaturated bydrocarbyl group of 1 to 15 carbon atoms containing 0 to 6 of hetero atoms, and $R_2$ independently a chain type or ring type saturated or unsaturated hydrocarbyl group of 1 to 15 carbon atoms containing 0 to 15 of hetero atoms, wherein, $R_1$ optionally has at least two bonding parts, and in the case that $R_1$ has at least two bonding parts, the rest parts except $R_1$ of the compounds represented by Formula 1 optionally connect to the $R_1$ to form a polymer structure; and crosslinking the composition for forming an organic anti-reflective coating layer coated on the etching layer.

* * * * *